(12) United States Patent
Chau et al.

(10) Patent No.: US 8,357,888 B2
(45) Date of Patent: Jan. 22, 2013

(54) PHOTOELECTRIC FEEDBACK SENSING SYSTEM HAVING A SENSING APPARATUS OUTPUTTING A LIGHT SIGNAL CORRESPONDING TO A CHARACTERISTIC OF A SAMPLE WITHIN THE SENSING APPARATUS

(75) Inventors: La-Kwan Chau, Chiayi (TW);
Szu-Shan Shieh, Taipei (TW);
Chin-Jung Kuo, Tainan County (TW);
Chung-Sheng Chiang, Tainan (TW);
Chang-Yue Chiang, Taiping (TW);
Yu-Shen Shih, Changhua County (TW)

(73) Assignee: National Chung Cheng University, Min-Hsiung Chia-Yi (TW)

( * ) Notice: Subject to any disclaimer, the term of this patent is extended or adjusted under 35 U.S.C. 154(b) by 330 days.

(21) Appl. No.: 12/925,101

(22) Filed: Oct. 14, 2010

(65) Prior Publication Data
US 2011/0278434 A1 Nov. 17, 2011

(30) Foreign Application Priority Data
May 14, 2010 (TW) ................................ 99115601 A

(51) Int. Cl.
*G01J 1/32* (2006.01)
(52) U.S. Cl. .................................... 250/205; 250/214 R

(58) Field of Classification Search .................. 250/205, 250/214 R, 559.4, 221; 315/149, 159, 156, 315/82; 327/514
See application file for complete search history.

(56) References Cited

U.S. PATENT DOCUMENTS
4,939,482 A * 7/1990 Nergaard et al. ............. 398/200

\* cited by examiner

*Primary Examiner* — Que T Le
(74) *Attorney, Agent, or Firm* — Hudak, Shunk & Farine, Co. LPA

(57) ABSTRACT

The present invention relates to a photoelectrical feedback sensing system. A first light signal passes through the sensing apparatus. A second light signal corresponding to a characteristic of a sample within the sensing apparatus is outputted from the sensing apparatus. The first photo detector receives the first light signal and outputs a first electric signal corresponding to the intensity of the first light signal. The second photo detector outputs a second electric signal corresponding to the intensity of the second light signal. A driving signal is generated by the micro-processor to drive the light-emitting unit. The micro-processor receives the second electric signal and converts the second electric signal into a digital signal. The feedback circuit modulates the driving signal for maintaining the optical stability of the first light signal so that the sensing system is less affected by environmental temperature fluctuation and noise interferences.

15 Claims, 10 Drawing Sheets

PHOTOELECTRIC FEEDBACK SENSING SYSTEM HAVING A SENSING APPARATUS OUTPUTTING A LIGHT SIGNAL CORRESPONDING TO A CHARACTERISTIC OF A SAMPLE WITHIN THE SENSING APPARATUS

FIELD OF THE INVENTION

The present invention relates to a photoelectrical sensing system, and more particularly to a photoelectrical sensing system with a feedback function.

BACKGROUND OF THE INVENTION

Presently, with the progress of biotechnology, the research of biological sensing becomes increasingly diversified. For example, the understanding of the characteristics such as DNA, RNA, enzymes and other proteins has a great benefit to biotechnology or medicine.

In current research of biological sensing system, many people focus on the changes between the characteristics of a biological sensing unit before and after various biological molecules are bound to the biological sensing unit, for example, the change in the optical characteristics of a biological sensing unit after an antibody, an antigen, or a DNA is bound to the corresponding antigen-, antibody- or DNA-functionalized biological sensing unit. In a method for measuring optical characteristics, light emitted from a light emitting diode or a laser can be used to interact with a biological sensing system and measurement is made for intensity changes or wavelength changes in the light after the interaction to estimate characteristics of biological samples. A method for measuring wavelength changes requires a bulky spectrometer, which is inconvenient to carry around and costly. A photo detection unit with a smaller volume and lower costs can be used in measuring changes in light intensity. The development of modern biological sensing is moving toward the trend of miniaturization. If the sensing method and operating performance of a biological sensing system can be designed simpler and more convenient to carry around for sensing purposes, the sensor will be greatly applicable.

In recent years the development of nano materials increasingly becomes a focus of research, and the industries such as optoelectronics, communications and medical instruments spend a lot of effort on the research and application of nano materials. Nano materials are so favored because nano materials provide properties completely different from the characteristics of the original materials. A free electron cloud on a noble metal nanoparticle surface is excited by an electromagnetic field with a specific frequency to produce a collective dipole resonance, but the oscillating electron cloud is restricted in the neighborhood of the nanoparticle, and thus such a resonance is called localized plasmon resonance (LPR). It is interesting to find that if the environmental refractive index around the noble metal nanoparticle changes, the frequency and the extinction cross-section of the LPR band will change accordingly. If the environmental refractive index around the noble metal nanoparticle increases, the localized plasmon resonance absorption band will shift to a longer wavelength and the absorption cross-section of the LPR band will increase. While observing the characteristics of scattered light, it can be found that when the environmental refractive index rises, the localized plasmon resonance scattering band also shifts to a longer wavelength and accompanied with an increase in the light intensity. Finally, modification is made for a specific recognition unit to provide a specific sensing ability. After the relationship between changes in the frequency or changes in the extinction cross-section of the resonance band and the concentrations of an analyte is analyzed, a calibration method is established. To enhance the change, noble metal nanoparticles are modified on an optical fiber to form a noble metal nanoparticle layer in this method. The above-mentioned noble metal nanoparticle layer is composed of one of noble metal nanospheres, noble metal nanosquares, noble metal nanocones, noble metal nanorods and noble metal nanoshells. Basically, the nanoparticles are not connected with each other. The noble metal is gold, silver or platinum. The characteristic that multiple total internal reflections take place in the optical waveguide is used to accumulate evanescent-wave absorption by the plasmon resonance of the noble metal nanoparticles, so as to enhance LPR signals and improve the sensing sensitivity. The sensing element developed by the combination of the optical waveguide substrate and the localized plasmon resonance principle, as described above, is called an optical waveguide-localized plasmon resonance (OW-LPR) sensor. If an optical fiber is used as the optical waveguide component, it is called a fiber optic-localized plasmon resonance (FO-LPR) sensor. If a tubular waveguide is used as the optical waveguide component, it is called a tubular waveguide-localized plasmon resonance (TW-LPR) sensor. If a planar waveguide is used as the optical waveguide component, it is called a planar waveguide-localized plasmon resonance (PW-LPR) sensor. After integration with a molecular or biological recognition unit, it has a sensing ability with high specificity and high sensitivity, so it has great potential to be developed as a sensing device for real-time detection.

Referring to FIG. 1, there is shown a schematic view of a prior art fiber optic-localized plasmon resonance biological sensing system. Light emitted from a light emitting diode or a laser B that is driven by a function generator A passes through a sensing optical fiber in a microfluidic component C, then the photodiode detector D receives and converts the passing light into an electric signal, which is sent to a lock-in amplifier E for analysis and demodulation, and then the computer F system displays the result after demodulation and analysis. However, due to the physical characteristics of light emitting diodes or lasers (including laser diodes), the intensity of light outputted from the light emitting diode or laser changes with age or difference in environmental temperature after being used for a period of time. Therefore, it is often unable to distinguish whether a signal change is caused by a is characteristic of a sample in the microfluidic component or by a change in the intensity of light outputted from the light-emitting unit itself during the detection. If light emitting diodes or lasers of special specifications and photoreceivers of special specifications are used, it is costly, complicated in operation and bulky in volume so that the cost of a biological sensing optical measuring system is significantly increased or it is difficult to miniaturize such system. Hence, the inventors design the photoelectrical feedback sensing system to improve the stability of a light emitting source.

SUMMARY OF THE INVENTION

In view of the above-mentioned problems of the prior art, an object of the present invention is to provide a photoelectrical feedback sensing system, which solves the problem of changes in the luminous intensity of a light source caused by environmental temperature fluctuation or aging or degradation of the light source.

According to the objective of the present invention, there is provided a photoelectrical feedback sensing system comprising a light-emitting unit, a sensing apparatus, a first photo detector, a second photo detector, a micro-processor and a feedback circuit.

The light-emitting unit can emit a first light signal. The first photo detector receives the first light signal and outputs a first electric signal corresponding to the intensity of the first light signal. The second photo detector receives the second light signal and outputs a second electric signal corresponding to the intensity of the second light signal. A driving signal is generated by the micro-processor to drive the light-emitting unit. The micro-processor is connected to the second photo detector to receive the second electric signal and converts the second electric signal into a digital signal. The feedback circuit is connected to the light-emitting unit, the first photo detector and the micro-processor to modulate the driving signal for maintaining the optical stability of the first light signal.

The first photo detector matches the second photo detector and both have similar temperature drift parameters.

The driving signal is a periodic square wave and serves as a synchronizing reference signal for modulation/demodulation and lock-in amplification.

The photoelectrical feedback sensing system further comprises a current-to-voltage conversion/amplification circuit connected between the first photo detector and the micro-processor to convert the second electric signal into a voltage signal and then to perform amplification.

The processor further comprises a driving signal generating unit, a lock-in amplification and demodulation circuit unit, and an analog-to-digital converting unit to receive the driving signal and the voltage signal after the secondary voltage amplification, to perform the lock-in amplification and synchronous demodulation on the voltage signal after the secondary voltage amplification by using the frequency of the driving signal as a reference value, and then to convert it into a digital signal.

The sensing apparatus is an optical waveguide-localized plasmon resonance (OW-LPR) sensor comprising an optical waveguide component and a noble metal nanoparticle layer, wherein the characteristic that multiple total internal reflections take place in the optical waveguide component is used to accumulate evanesecent-wave absorption by the plasmon resonance of the noble metal nanoparticle layer.

The sensing apparatus is a fiber optic-localized plasmon resonance (FO-LPR) sensor comprising an optical fiber component and a noble metal nanoparticle layer, wherein the characteristic that multiple total internal reflections take place in the optical fiber component is used to accumulate evanesecent-wave absorption by the plasmon resonance of the noble metal nanoparticle layer.

The sensing apparatus is a tubular waveguide-localized plasmon resonance (TW-LPR) sensor comprising a tubular waveguide component and a noble metal nanoparticle layer, wherein the characteristic that multiple total internal reflections take place in the tubular waveguide component is used to accumulate evanesecent-wave absorption by the plasmon resonance of the noble metal nanoparticle layer.

The sensing apparatus is a planar waveguide-localized plasmon resonance (PW-LPR) sensor comprising a planar waveguide component and a noble metal nanoparticle layer, wherein the characteristic that multiple total internal reflections take place in the planar waveguide component is used to accumulate evanesecent-wave absorption by the plasmon resonance of the noble metal nanoparticle layer.

As described above, the photoelectrical feedback sensing system of the present invention may have one or more of the following advantages:

(1) The photoelectrical feedback sensing system utilizes the feedback circuit to allow the light-emitting unit to output the first light signal with stable intensity, thus to solve the problem of the unstable light intensity caused by temperature fluctuation or aging or degradation of the light-emitting unit.

(2) Common, commercially available light emitting diodes or lasers and common photo detectors can be used in the photoelectrical feedback sensing system, thus to solve the problem of significantly increased cost caused by the necessary use of light-emitting units or photo detectors of special specifications.

(3) The first photo detector matches the second photo detector, so as to provide a good luminous flux and effectively compensate for the influence of temperature changes.

(4) The driving signal is a periodic modulated square wave, which can protect against noise interferences when it is in corporation with a lock-in amplification circuit.

DETAILED DESCRIPTION OF THE PREFERRED EMBODIMENTS

Figure 2:
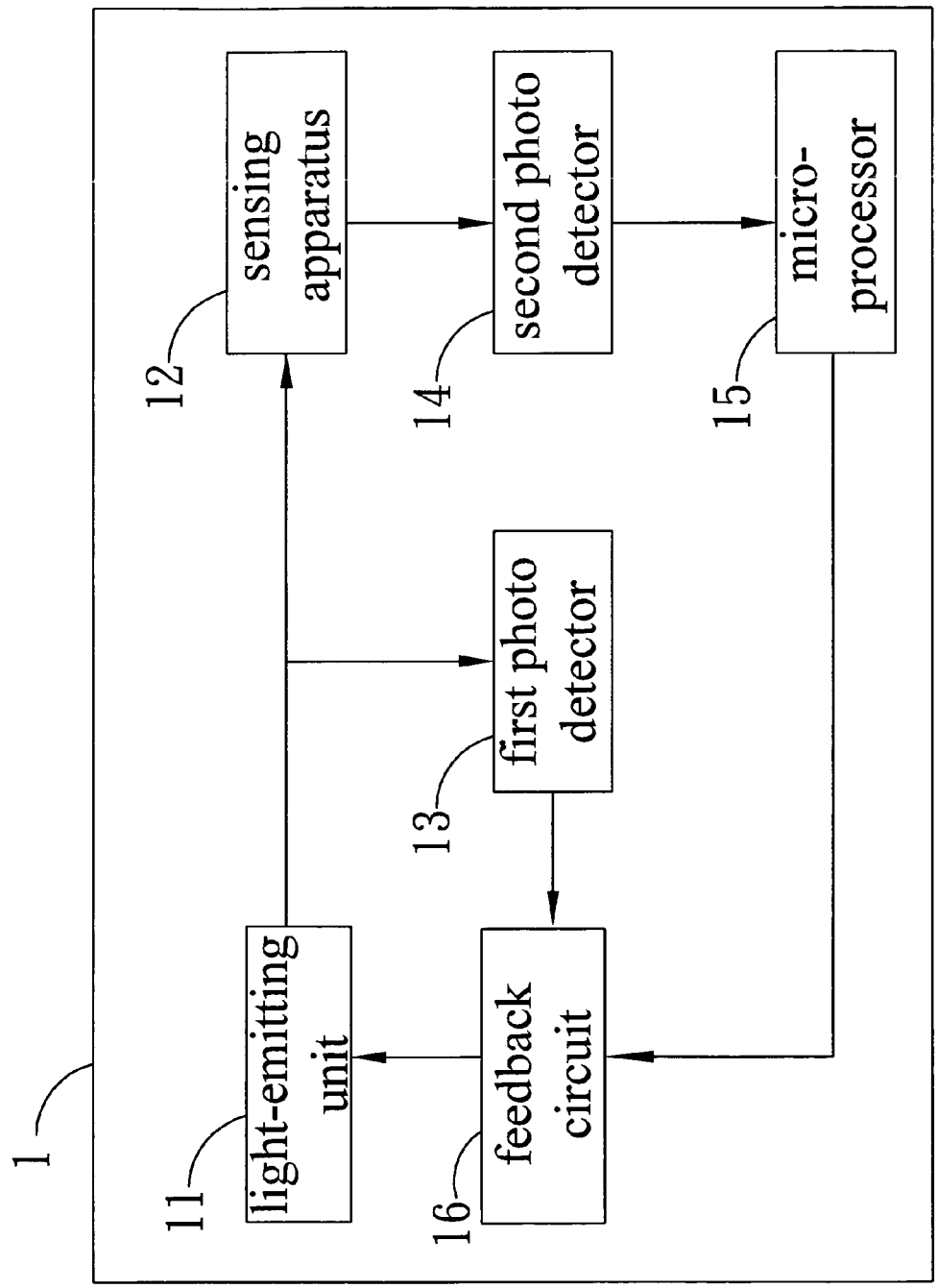
FIG. 2 is a block diagram of a first embodiment of a photoelectrical feedback sensing system according to the present invention.

Referring to FIG. 2, there is shown a block diagram of a first embodiment of a photoelectrical feedback sensing system according to the present invention. In this figure, the photoelectrical feedback sensing system 1 according to the present invention comprises a light-emitting unit 11, a sensing apparatus 12, a first photo to detector 13, a second photo detector 14, a micro-processor 15 and a feedback circuit 16.

A first light signal can be emitted from the light-emitting unit 11 to pass through the sensing apparatus 12. A second light signal corresponding to a characteristic of a sample in the sensing apparatus 12 is outputted from the sensing apparatus 12. The light-emitting unit 11 is preferably a light emitting diode (LED). The sensing apparatus 12 preferably comprises a sensing optical fiber in a microfluidic component, and is used for sensing biological or chemical molecules. The sensing apparatus 12 is provided thereon with a noble metal nanoparticle layer comprising a plurality of noble metal nanoparticles.

The sensing apparatus may be an optical waveguide-localized plasmon resonance (OW-LPR) sensor comprising an optical waveguide component and a noble metal nanoparticle layer, wherein the characteristic that multiple total internal reflections take place in the optical waveguide component is utilized to accumulate evanesecent-wave absorption by the plasmon resonance of the noble metal nanoparticle layer.

The sensing apparatus may be a fiber optic-localized plasmon resonance (FO-LPR) sensor comprising an optical fiber component and a noble metal nanoparticle layer, wherein the characteristic that multiple total internal reflections take place in the optical fiber component is utilized to accumulate evanesecent-wave absorption by the plasmon resonance of the noble metal nanoparticle layer.

The sensing apparatus may be a tubular waveguide-localized plasmon resonance (TW-LPR) sensor comprising a tubular waveguide component and a noble metal nanoparticle layer, wherein the characteristic that multiple total internal reflections take place in the tubular waveguide component is utilized to accumulate evanesecent-wave absorption by the plasmon resonance of the noble metal nanoparticle layer.

The sensing apparatus may be a planar waveguide-localized plasmon resonance (PW-LPR) sensor comprising a planar waveguide component and a noble metal nanoparticle layer, wherein the characteristic that multiple total internal reflections take place in the planar waveguide component is utilized to accumulate evanesecent-wave absorption of the plasmon resonance by the noble metal nanoparticle layer.

The first photo detector 13 receives the first light signal and outputs a first electric signal corresponding to the intensity of the first light signal. The second photo detector 14 receives the second light signal and outputs a second electric signal corresponding to the intensity of the second light signal. Preferably, the first photo detector 13 and the second photo detector 14 are photodiode detectors or phototransistor detectors. The temperature drift parameters of the first photo detector 13 match that of the second photo detector 14, that is, environmental temperature affecting on the first photo detector 13 is the same as that on the second photo detector 14.

A driving signal is generated by the micro-processor 15. The driving signal is preferably a periodic square wave, and the frequency of the square wave is preferably between 1,000 Hz and 20,000 Hz. Furthermore, the micro-processor 15 is connected to the second photo detector 14 to receive the second electric signal and converts the second electric signal into a digital signal after digital processing.

The feedback circuit 16 is connected to the light-emitting unit 11, the first photo detector 13 and the micro-processor 15, whereby the driving signal is controlled in a feedback manner by monitoring the first electric signal to modulate the light-emitting unit 11, so that the light-emitting unit 11 outputs the first light signal with stable intensity during the reception of the driving signal to allow the light-emitting unit 11 to emit light at an intensity approximate to the preset intensity. If the environmental temperature changes, the electric signals outputted from the first photo detector 13 and the second photo detector 14 change due to environmental temperature changes. However, the first photo detector 13 and the second photo detector 14 have similar temperature drift parameters, thus compensating for the influence caused by environmental temperature changes. The feedback circuit is preferably an auto gain control (AGC) circuit.

Figure 3:
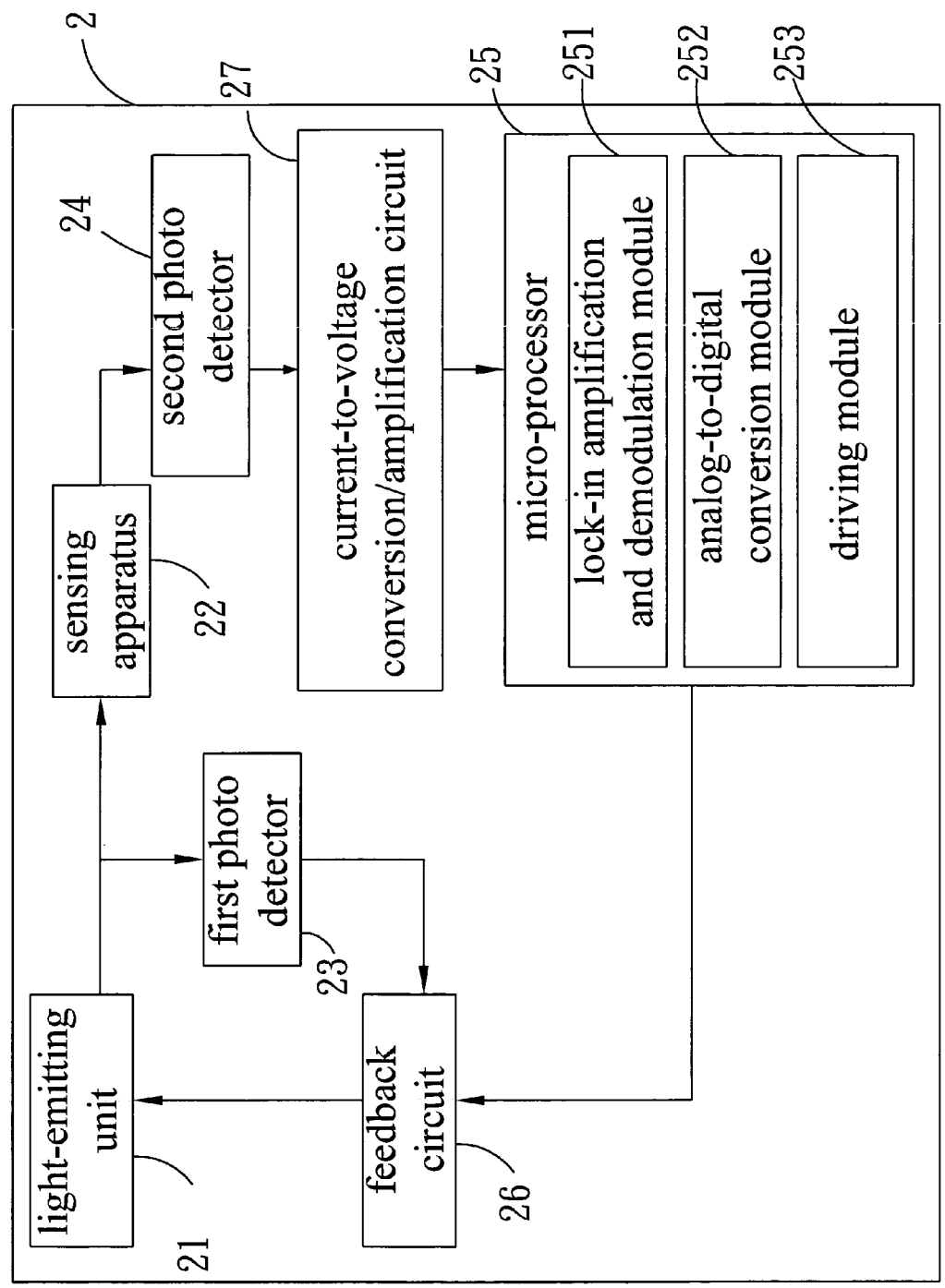
FIG. 3 is a block diagram of a second embodiment of a photoelectrical feedback sensing system according to the present invention.

Referring to FIG. 3, there is shown a block diagram of a second embodiment of a photoelectrical feedback sensing system according to the present invention. As compared with the first embodiment, the difference is that a to current-to-voltage conversion/amplification circuit 27 is further cascaded between the second photo detector 24 and the micro-processor 25 while the micro-processor 25 further comprises a lock-in amplification and demodulation module 251, an analog-to-digital conversion module 252 and a driving module 253. The other parts are similar to those in the first embodiment, and will be explained in no more details.

Figure 4:
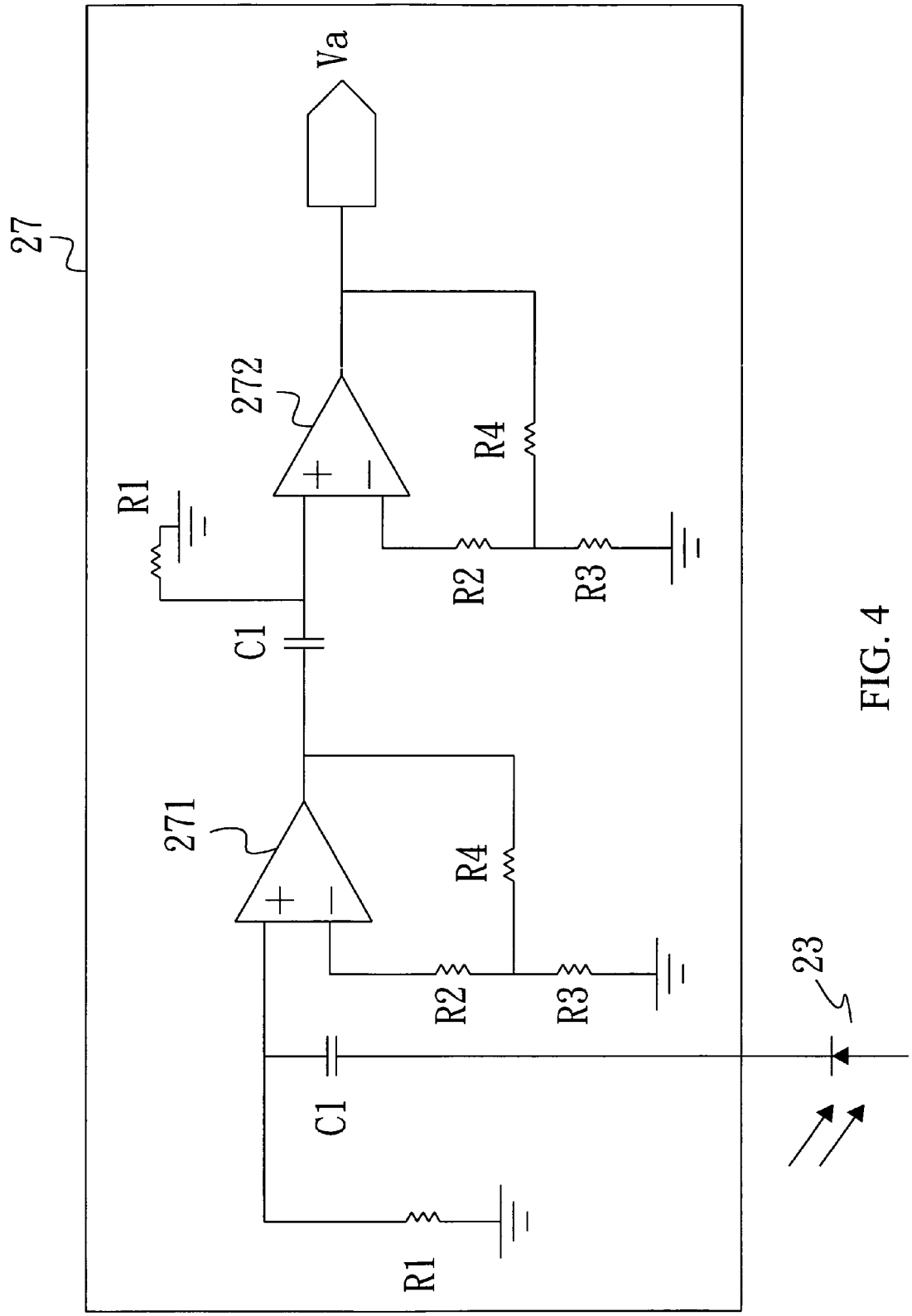
FIG. 4 is a schematic view of the current-to-voltage conversion/amplification circuit of FIG. 3.

Referring to FIG. 4, there is shown a schematic view of the current-to-voltage conversion/amplification circuit of FIG. 3. In this figure, the current-to-voltage conversion/amplification circuit 27 comprises a primary operational amplifier 271, a secondary operational amplifier 272, two first capacitors C1, two first resistors R1, two second resistors R2, two third resistors R3 and two fourth resistors R4. The first capacitors C1 and the first resistors R1 are respectively connected in parallel to the positive input ends of the primary operational amplifier 271 and the secondary operational amplifier 272 to filter high-frequency noises. The second resistors R2, the third resistors R3 and the fourth resistors R4 are used for controlling the feedback gains of the primary operational amplifier 271 and the secondary operational amplifier 272. The second electric signal is a current signal. In the current-to-voltage conversion/amplification circuit 27, the primary operational amplifier 271 amplifies and converts the second electric signal from a current signal into a voltage signal to complete the primary voltage amplification, and then a secondary operational amplifier performs the secondary voltage amplification of the voltage signal. Then the secondary operational amplifier 272 amplifies the voltage signal once again and outputs it to the node Va to complete the secondary voltage amplification.

The micro-processor 25 is connected to the node Va to receive the voltage signal after the secondary voltage amplification from the current-to-voltage conversion/amplification circuit 27 and utilizes the lock-in amplification and demodulation module 251 to perform the lock-in amplification and synchronous demodulation on the portion of the voltage signal after the secondary voltage amplification, which has the same frequency as that of the driving signal, by using the frequency of the driving signal generated by the driving module 253 as a reference value. Then the analog-to-digital conversion module 252 converts the demodulated signal into a digital signal. The analog signal may be displayed on a display apparatus or an electronic apparatus connected with the micro-processor 25 to provide experimental data. The driving module 253 allows the demodulated driving signal to be transmitted to the feedback circuit 26 and the lock-in amplification and demodulation module 251.

The feedback circuit 26 is connected to the light-emitting unit 21, the first photo detector 23 and the micro-processor 25. The feedback circuit 26 receives the first electric signal and the driving signal. The feedback circuit 26 controls the driving signal in a feedback manner by monitoring the first electric signal to modulate the light-emitting unit 21, so that the light-emitting unit 21 outputs the first light signal with stable intensity during the reception of the driving signal. When the intensity of the first light signal decreases, the feedback circuit 26 increases the voltage value of the input driving signal. When the intensity of the first light signal increases, the feedback circuit 26 decreases the voltage value of the input driving signal to maintain the optical stability of the first light signal emitted by the light-emitting unit 21.

Figure 1:
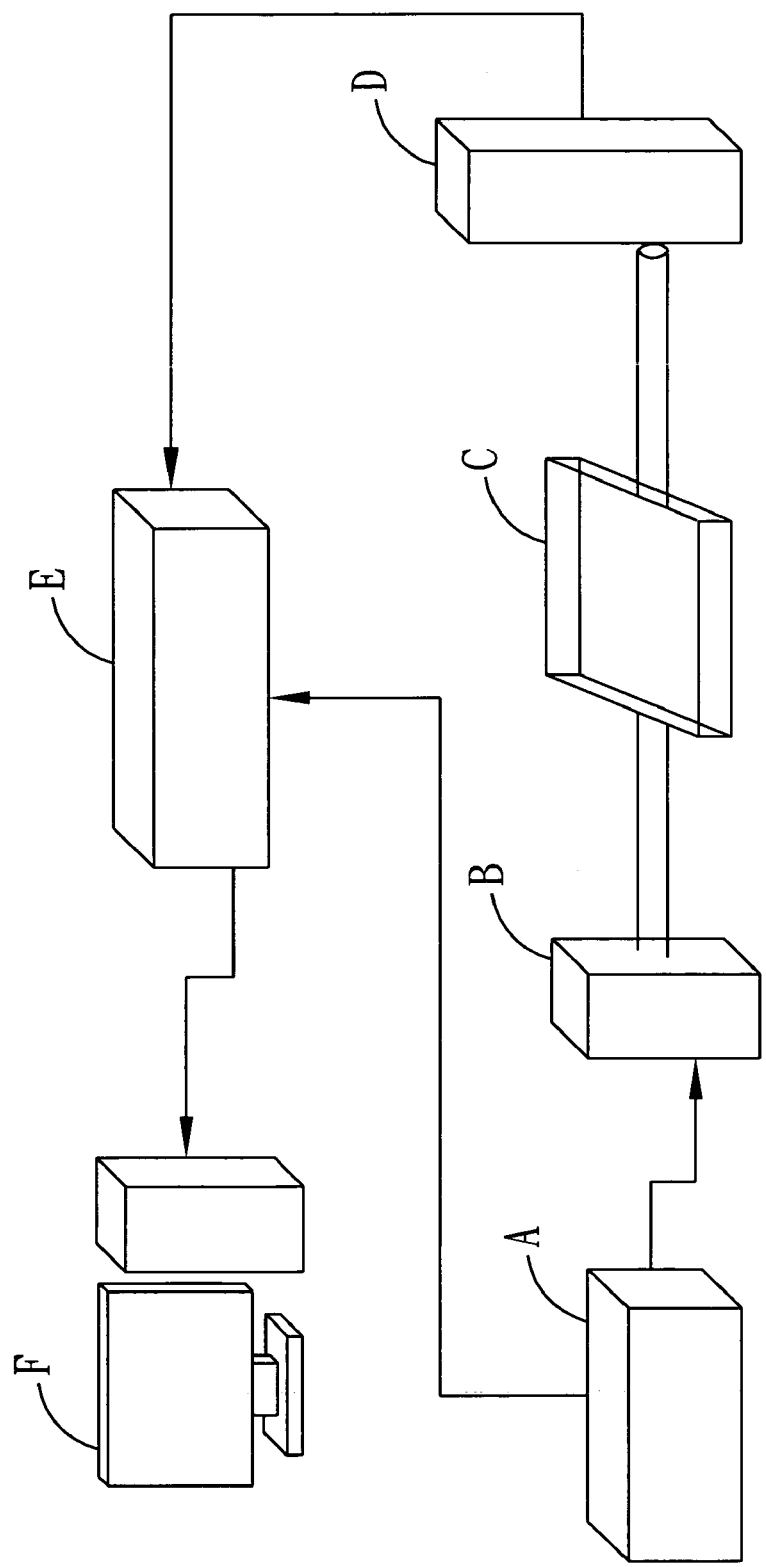
FIG. 1 is a schematic view of a prior art fiber optic-localized plasmon resonance biological sensing system.
Figure 5:
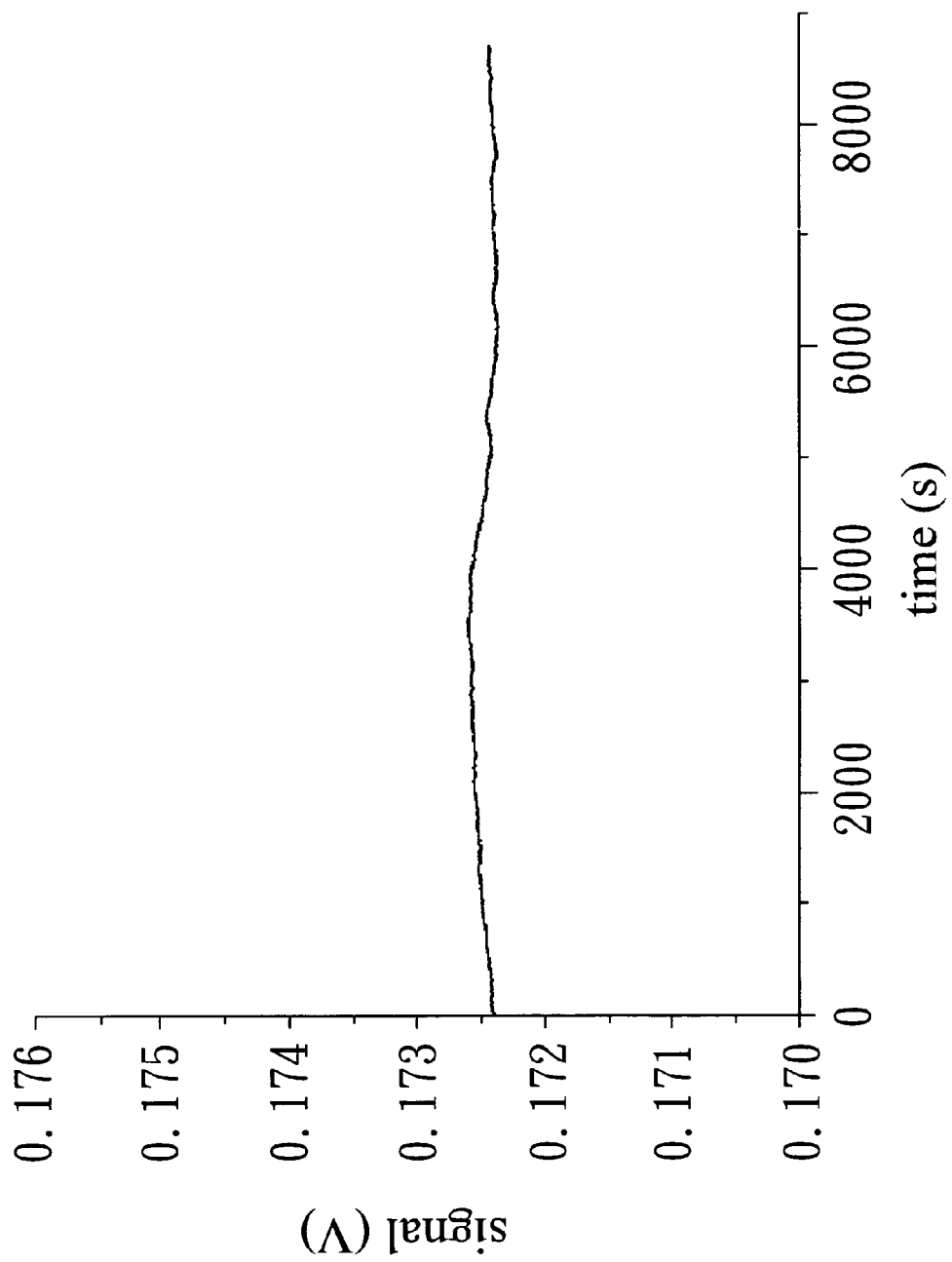
FIG. 5 is a diagram showing the intensity of the light source of FIG. 1 with respect to time.

Referring to FIG. 5, there is shown a diagram showing the intensity of the light source of FIG. 1 with respect to time. In this figure, the prior art fiber optic-localized plasmon resonance biological sensing system is an open-loop system. The intensity of the light source fluctuates significantly after the light emitting diode B has been driven by the function generator A for a period of time. As a result, the computer F system is difficult to separate the signal change caused by the bio-recognition event occurring on the sensing optical fiber in the microfluidic component C from the fluctuation of light source intensity.

Figure 6:
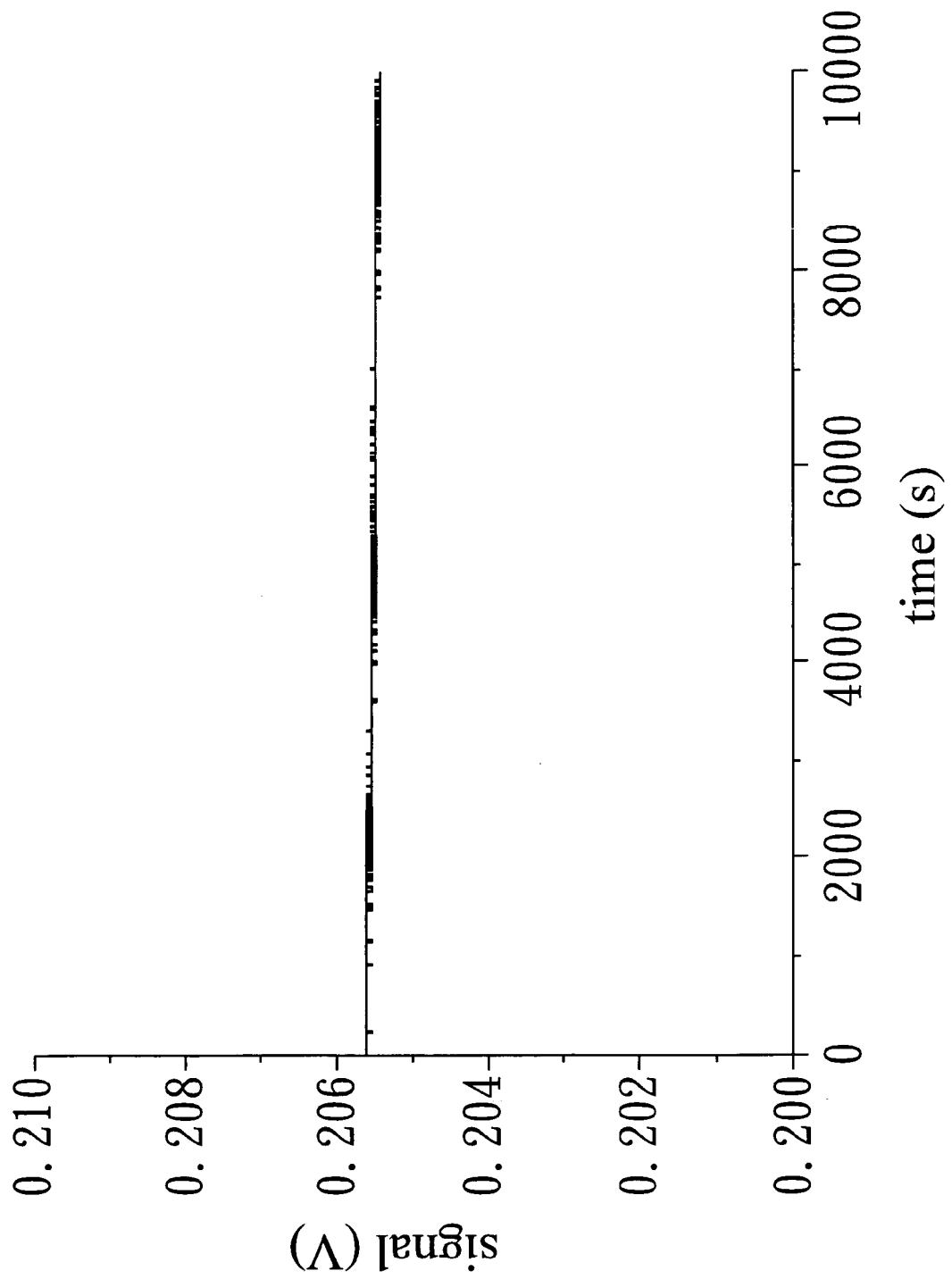
FIG. 6 is a diagram of the first electric signal of a second embodiment of a photoelectrical feedback sensing system with respect to time according to the present invention after feedback.

Also referring to FIG. 6, there is shown a diagram of the intensity of the light source of a second embodiment of a photoelectrical feedback sensing system with respect to time according to the present invention after feedback. In this figure, the intensity of the first light signal is substantially stable with respect to time, unlike the intensity of the light signal as shown in FIG. 5, which fluctuates with time. The intensity of the light signal has peak-to-peak stability of 0.073% and the relative standard deviation (RSD) of the stability can be kept at 0.022%.

Figure 7A:
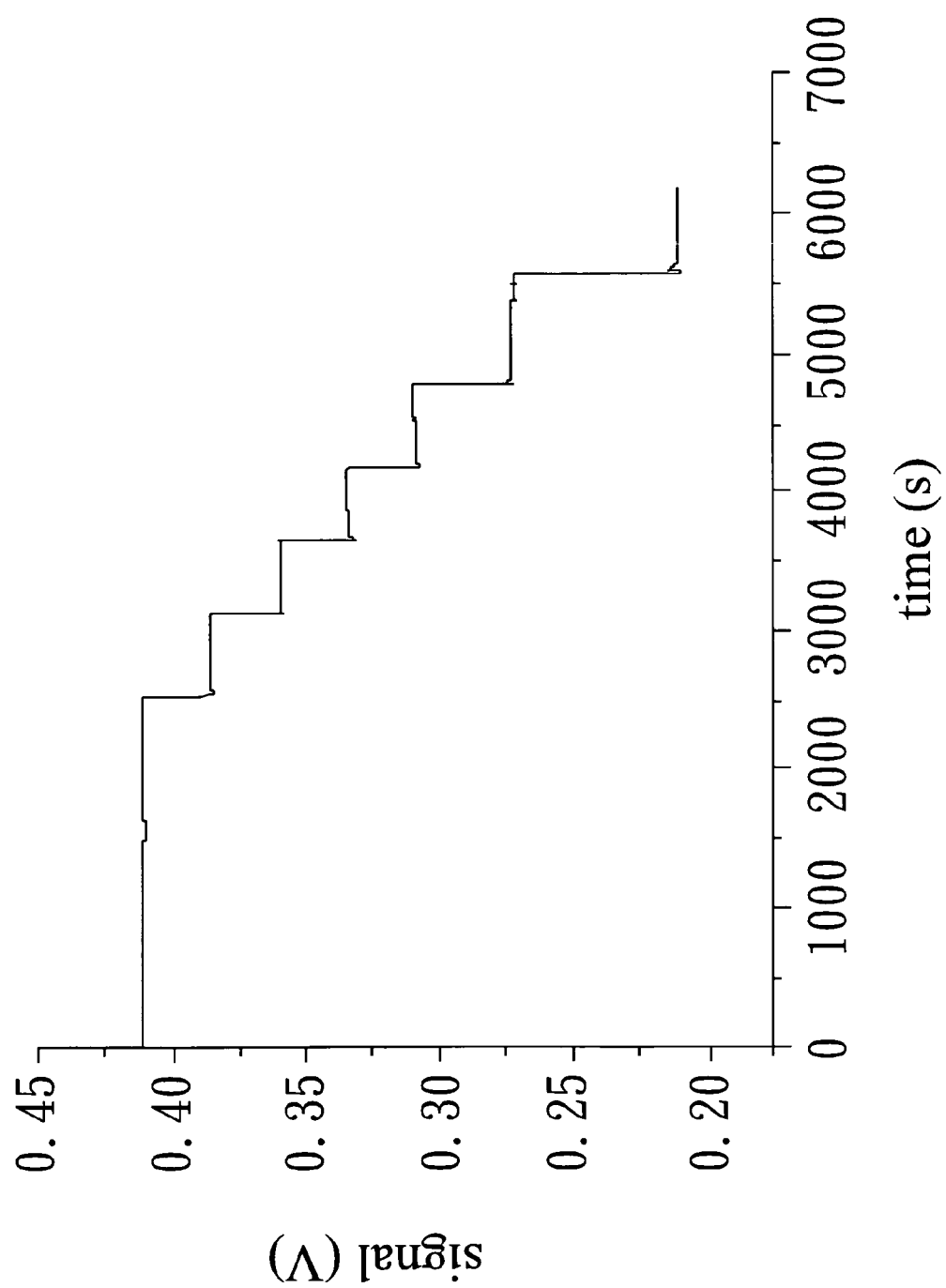
FIG. 7A is a diagram of the signal intensity obtained at different concentrations of sucrose solutions by a second embodiment of a photoelectrical feedback sensing system according to the present invention.
Figure 7B:
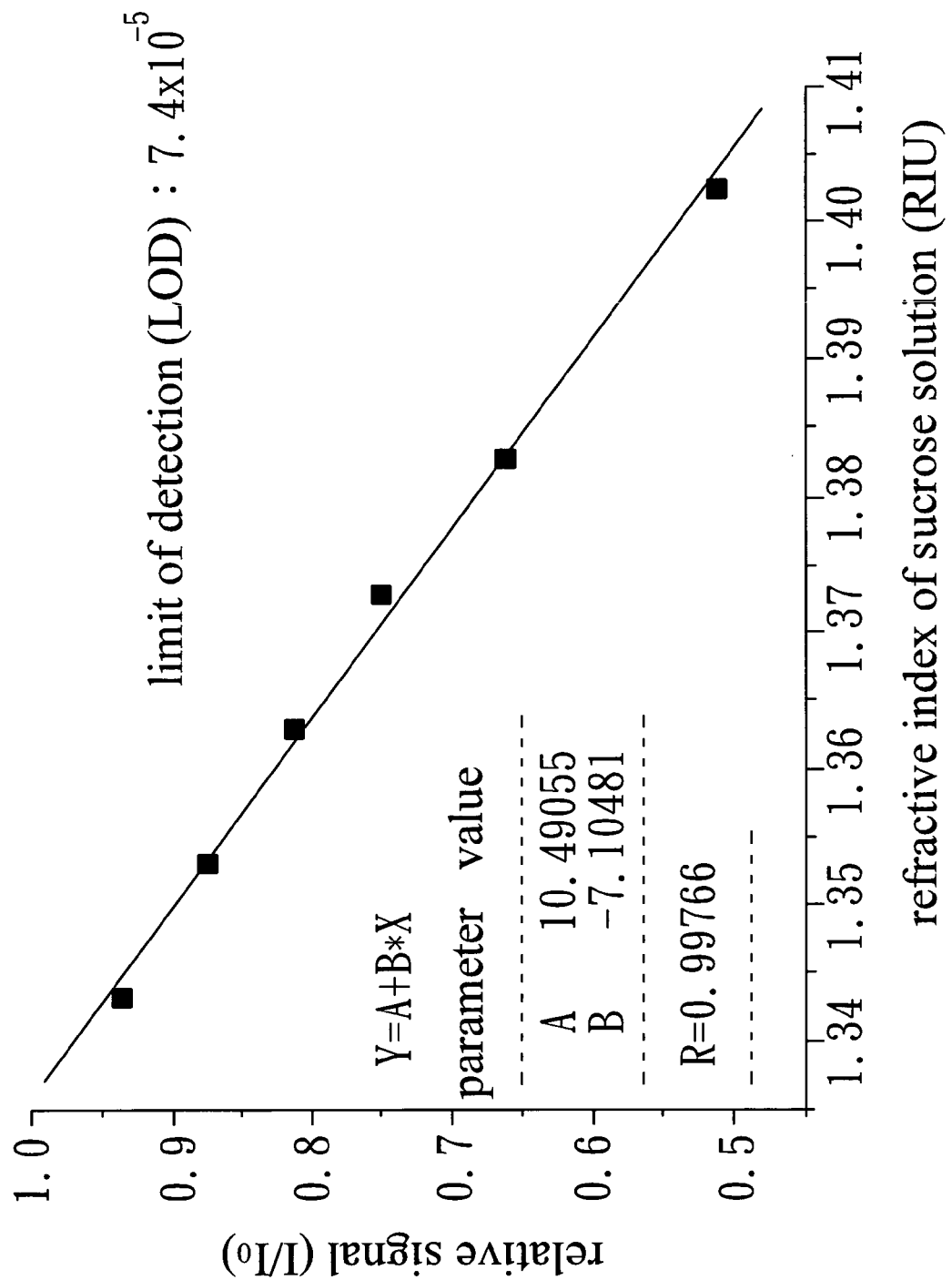
FIG. 7B is a graph showing the relative signal ($I/I_0$) vs. refractive index obtained at different concentrations of sucrose solutions by a second embodiment of a photoelectrical feedback sensing system according to the present invention.

Referring to FIG. 7, it shows the effect of the solution refractive index on the sensor signal by a second embodiment of a photoelectrical feedback sensing to system according to the present invention. The refractive index of solution changes at different concentrations of sucrose solutions. A diagram of the signal intensity at additions of sucrose solutions of different refractive indexes (FIG. 7A) and the corresponding calibration curve (FIG. 7B) are obtained by using a localized plasmon resonance sensing optical fiber. In FIG. 7B, I represents a sensor signal at different sucrose concentrations and $I_0$ represents the sensor signal of a blank. The result exhibits a good linear relationship between the relative sensor signal ($I/I_0$) and the refractive index of the solution with an R value of 0.997 and with a refractive index resolution of $7.4 \times 10^{-5}$ RIU, which is better than the refractive index resolution obtained by the prior art sensing system.

Figure 8A:
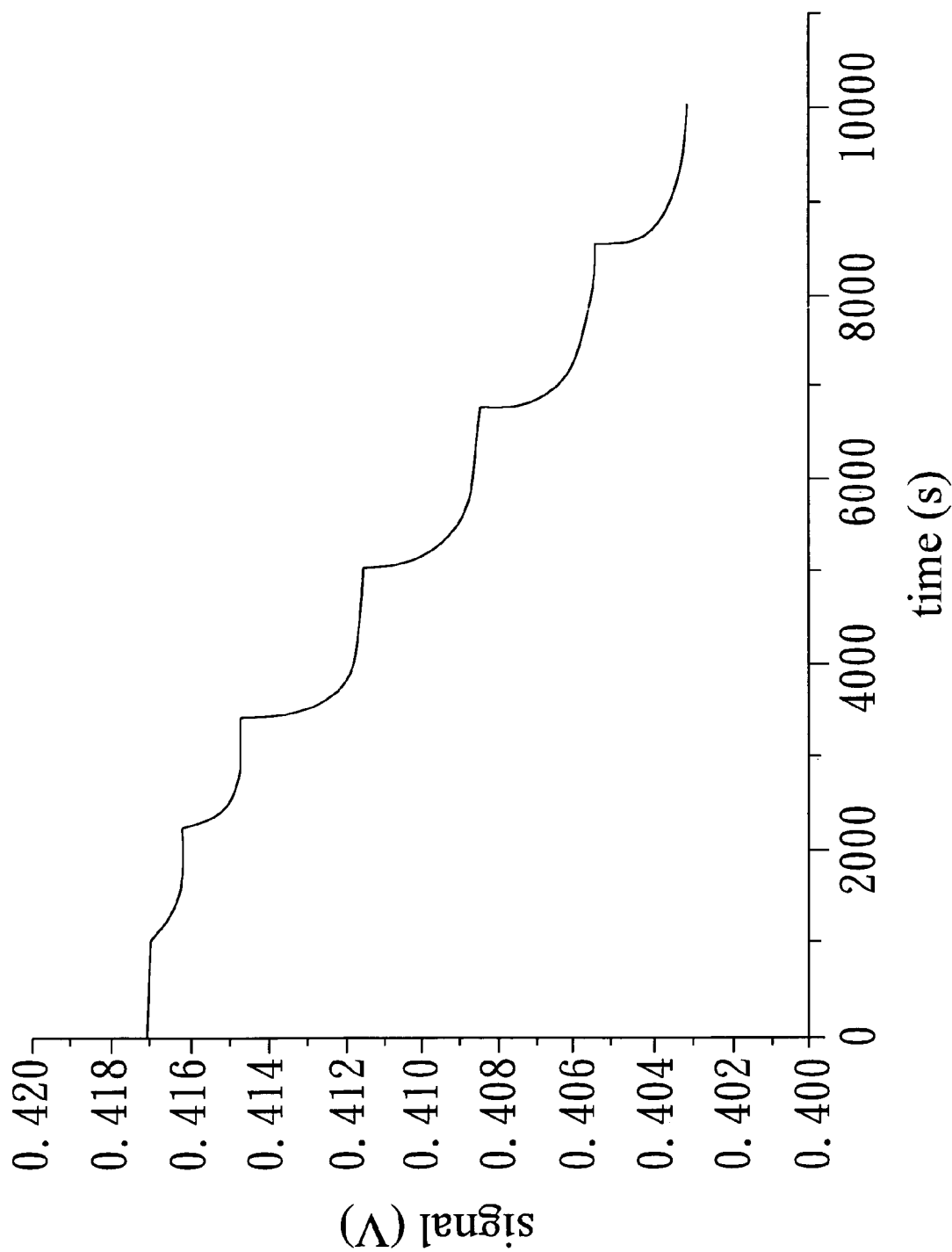
FIG. 8A is a diagram of the signal intensity obtained at different concentrations of anti-DNP solutions by a second embodiment of a photoelectrical feedback sensing system according to the present invention.
Figure 8B:
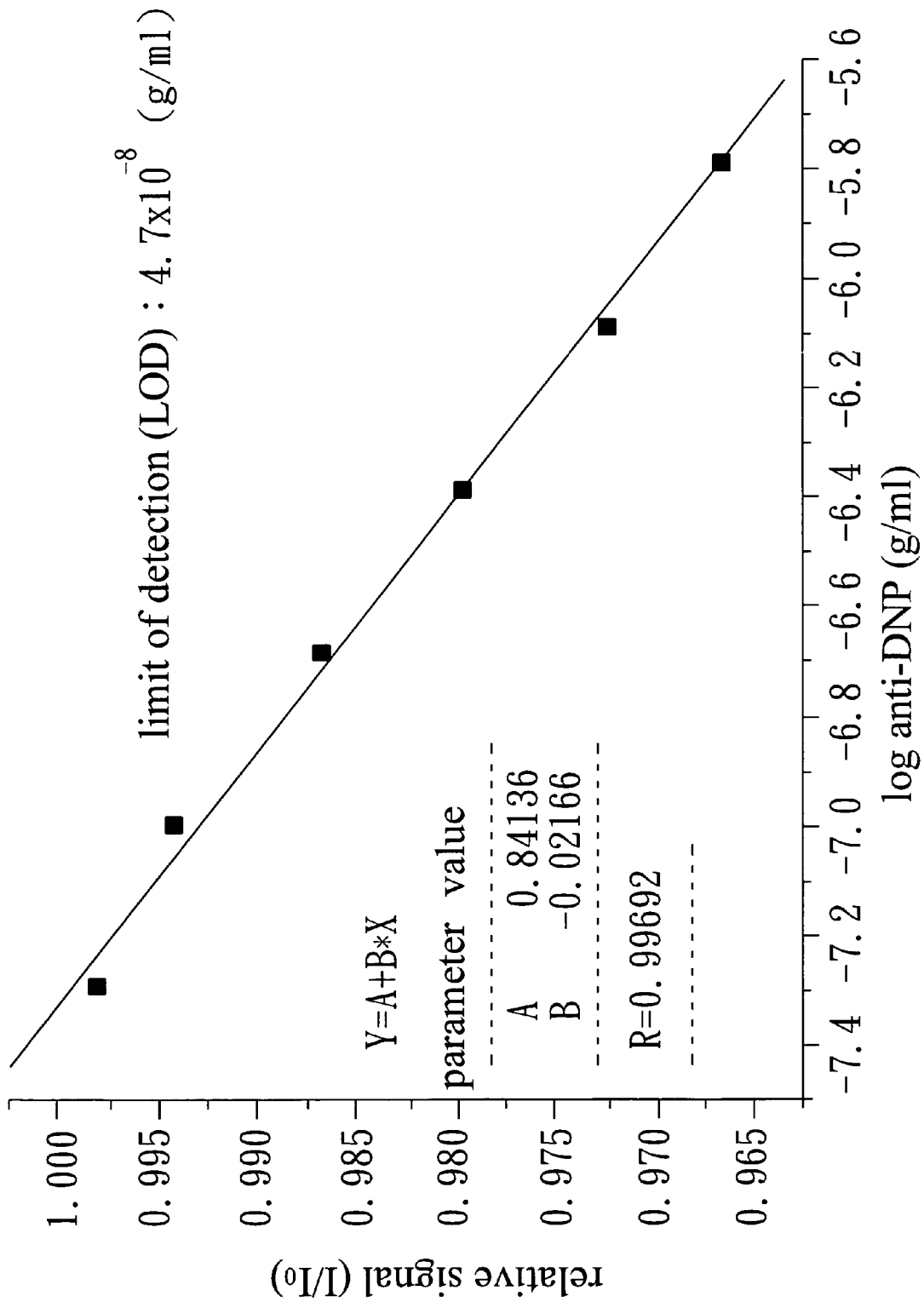
FIG. 8B is a graph showing the relative signal ($I/I_0$) vs. logarithmic concentration of anti-DNP solutions at different concentrations of anti-DNP by a second embodiment of a photoelectrical feedback sensing system according to the present invention.

Referring to FIG. 8, it shows the experimental result of the detection of the biochemical samples by a second embodiment of a photoelectrical feedback sensing system according to the present invention. A DNP-functionalized localized plasmon resonance sensing optical fiber is used to detect anti-DNP at different concentrations. It can be clearly seen from FIG. 8A that the drops in the sensor signals in an exponential manner are mainly caused by the binding reaction of DNP and anti-DNP and represent a kinetic curve of the molecular binding. The data analysis as shown in FIG. 8B plots the relative sensor signal ($I/I_0$) vs. logarithmic concentration of anti-DNP and yields an R value of 0.997. In FIG. 8B, I represents a sensor signal at different anti-DNP concentrations and $I_0$ represents the sensor signal of a blank. The limit of detection is estimated as $3.8 \times 10^{-11}$ M, which is better than the limit of detection obtained by the prior art sensing system.

The above description is illustrative only and is not to be considered limiting. Various modifications or changes can be made without departing from the spirit and scope of the invention. All such equivalent modifications and changes shall be included within the scope of the appended claims.

What is claimed is:

1. A photoelectrical feedback sensing system comprising:
   a light-emitting unit arranged for emitting a first light signal;
   a sensing apparatus arranged for receiving the first light signal and outputting a second light signal corresponding to a characteristic of a sample within the sensing apparatus;
   a first photo detector arranged for receiving the first light signal and outputting a first electric signal corresponding to intensity of the first light signal;
   a second photo detector arranged for receiving the second light signal and outputting a second electric signal corresponding to intensity of the second light signal;
   a micro-processor arranged for generating a driving signal, being connected to the second photo detector to receive the second electric signal, and converting the second electric signal into a digital signal; and
   a feedback circuit connected to the light-emitting unit, the first photo detector and the micro-processor to modulate the driving signal for maintaining optical stability of the first light signal.

2. The photoelectrical feedback sensing system of claim 1, wherein the first photo detector and the second photo detector are matched in temperature drift parameters, such that an effect of environmental temperature on the first photo detector is the same as on the second photo detector.

3. The photoelectrical feedback sensing system of claim 1, wherein the driving signal is a periodical square wave.

4. The photoelectrical feedback sensing system of claim 3, wherein the periodical square wave has a frequency between 1 kHz and 20 kHz.

5. The photoelectrical feedback sensing system of claim 1, wherein the photoelectrical feedback sensing system further comprises a current-to-voltage conversion/amplification circuit connected between the second photo detector and the micro-processor to convert the second electric signal into a voltage signal and then to perform amplification.

6. The photoelectrical feedback sensing system of claim 5, wherein in the current-to-voltage conversion/amplification circuit, a primary operational amplifier converts the first electric signal from a current signal into the voltage signal and performs a primary voltage amplification, and then a secondary operational amplifier performs a secondary voltage amplification of the voltage signal.

7. The photoelectrical feedback sensing system of claim 6, wherein the micro-processor further comprises a lock-in amplification and demodulation module, and the lock-in amplification and demodulation module receives the voltage signal after the secondary voltage amplification and performs a lock-in amplification and synchronous demodulation on the voltage signal after the secondary voltage amplification by using a frequency of the driving signal as a synchronizing reference value.

8. The photoelectrical feedback sensing system of claim 7, wherein the micro-processor further comprises an analog-to-digital conversion module and a driving module, for converting the voltage signal after the lock-in amplification and synchronous demodulation into the digital signal and generating the driving signal, respectively.

9. The photoelectrical feedback sensing system of claim 1, wherein the feedback circuit is an auto gain control (AGC) circuit.

10. The photoelectrical feedback sensing system of claim 1, wherein the sensing apparatus comprises a sensing optical fiber in a microfluidic component.

11. The photoelectrical feedback sensing system of claim 1, wherein the light-emitting unit is a light emitting diode or a laser.

12. The photoelectrical feedback sensing system of claim 1, wherein the sensing apparatus is an optical waveguide-localized plasmon resonance (OW-LPR) sensor comprising an optical waveguide component and a noble metal nanoparticle layer and wherein a characteristic that multiple total internal reflections take place in the optical waveguide component is utilized to accumulate evanesecent-wave absorption by plasmon resonance of the noble metal nanoparticle layer.

13. The photoelectrical feedback sensing system of claim 1, wherein the sensing apparatus is a fiber optic-localized plasmon resonance (FO-LPR) sensor comprising an optical fiber component and a noble metal nanoparticle layer and wherein a characteristic that multiple total internal reflections take place in the optical fiber component is utilized to accumulate evanesecent-wave absorption by plasmon resonance of the noble metal nanoparticle layer.

14. The photoelectrical feedback sensing system of claim 1, wherein the sensing apparatus is a tubular waveguide-localized plasmon resonance (TW-LPR) sensor comprising a tubular waveguide component and a noble metal nanoparticle layer and wherein a characteristic that multiple total internal reflections take place in the tubular waveguide component is utilized to accumulate evanesecent-wave absorption by plasmon resonance of the noble metal nanoparticle layer.

15. The photoelectrical feedback sensing system of claim 1, wherein the sensing apparatus is a planar waveguide-localized plasmon resonance (PW-LPR) sensor comprising a planar waveguide component and a noble metal nanoparticle layer and wherein a characteristic that multiple total internal reflections take place in the planar waveguide component is utilized to accumulate evanesecent-wave absorption by plasmon resonance of the noble metal nanoparticle layer.

* * * * *

UNITED STATES PATENT AND TRADEMARK OFFICE
CERTIFICATE OF CORRECTION

PATENT NO. : 8,357,888 B2
APPLICATION NO. : 12/925101
DATED : January 22, 2013
INVENTOR(S) : Lai-Kwan Chau et al.

It is certified that error appears in the above-identified patent and that said Letters Patent is hereby corrected as shown below:

Title page, item (75) Inventors: should read "Lai-Kwan Chau".

Signed and Sealed this
Second Day of April, 2013

Teresa Stanek Rea
*Acting Director of the United States Patent and Trademark Office*